(12) United States Patent
Londt et al.

(10) Patent No.: US 9,622,717 B2
(45) Date of Patent: Apr. 18, 2017

(54) SYSTEMS AND METHODS FOR ADAPTIVE COMPUTED TOMOGRAPHY ACQUISITION

(71) Applicant: General Electric Company, Schenectady, NY (US)

(72) Inventors: John Howard Londt, Oconomowoc, WI (US); Roy A. Nilsen, Waukesha, WI (US); Holly Ann McDaniel, Waukesha, WI (US); Scott D. Slavic, Sussex, WI (US); John Irvin Jackson, Waukesha, WI (US); Elizabeth Nett, Waukesha, WI (US); Ann Soderman, Waukesha, WI (US); Victor Eduardo McCormack, Westborough, MA (US)

(73) Assignee: General Electric Company, Schenectady, NY (US)

( * ) Notice: Subject to any disclaimer, the term of this patent is extended or adjusted under 35 U.S.C. 154(b) by 307 days.

(21) Appl. No.: 14/575,390

(22) Filed: Dec. 18, 2014

(65) Prior Publication Data
US 2016/0174926 A1 Jun. 23, 2016

(51) Int. Cl.
| | | |
|---|---|---|
| *A61B 6/00* | (2006.01) | |
| *A61B 6/03* | (2006.01) | |
| *A61B 5/0245* | (2006.01) | |
| *A61B 5/024* | (2006.01) | |
| *A61B 5/00* | (2006.01) | |
| *A61B 5/0456* | (2006.01) | |
| *A61B 5/0464* | (2006.01) | |
| *A61B 5/0472* | (2006.01) | |
| *A61B 5/08* | (2006.01) | |

(52) U.S. Cl.
CPC .......... *A61B 6/5288* (2013.01); *A61B 5/0245* (2013.01); *A61B 5/7285* (2013.01); *A61B 6/032* (2013.01); *A61B 6/503* (2013.01); *A61B 6/541* (2013.01); *A61B 5/02405* (2013.01); *A61B 5/0456* (2013.01); *A61B 5/0464* (2013.01); *A61B 5/0472* (2013.01); *A61B 5/0816* (2013.01); *A61B 5/704* (2013.01)

(58) Field of Classification Search
CPC .. A61B 6/00; A61B 6/03; A61B 6/032; A61B 6/035; A61B 6/10; A61B 6/541; A61B 6/542; A61B 6/503; A61B 6/5288; A61B 5/0245; A61B 5/024; A61B 5/02405
USPC ........................................... 378/4, 8
See application file for complete search history.

(56) References Cited

U.S. PATENT DOCUMENTS

| | | | |
|---|---|---|---|
| 5,206,807 A | 4/1993 | Hatke et al. | |
| 6,937,696 B1* | 8/2005 | Mostafavi | A61B 5/7292 378/65 |

(Continued)

FOREIGN PATENT DOCUMENTS

| | | |
|---|---|---|
| EP | 1354554 A2 | 10/2003 |
| WO | 2011048547 A1 | 4/2011 |

*Primary Examiner* — Jurie Yun
(74) *Attorney, Agent, or Firm* — Dean D. Small; The Small Patent Law Group, LLC

(57) ABSTRACT

Methods and systems are provided that obtain a scan prescription and receive physiologic feature or interest (FOI) measurements of an object of interest during a scan time. The methods and systems further compare at least one of the received physiologic FOI measurements with a predetermined threshold range, and determine a scan setting by evaluating an acquisition rule set based on the physiologic FOI measurement.

20 Claims, 4 Drawing Sheets

(56) References Cited

U.S. PATENT DOCUMENTS

2008/0063137 A1 3/2008 Hsieh et al.
2014/0098932 A1 4/2014 Profio et al.

* cited by examiner

SYSTEMS AND METHODS FOR ADAPTIVE COMPUTED TOMOGRAPHY ACQUISITION

BACKGROUND OF THE INVENTION

The subject matter disclosed herein relates generally to systems and methods for computed tomography (CT) imaging.

In CT imaging, an X-ray source may be rotated around an object of interest (e.g., a patient, organ of a patient) to obtain imaging information. The object of interest is injected with a contrast agent (e.g., radiocontrast agent, an ionic contrast agent, a barium sulfate contrast agent, a blood agent) to provide maximum contrast in the imaging information. X-rays emitted from the X-ray source, attenuated by the object of interest, may be collected or detected by a detector and used to reconstruct an image. The X-rays may be emitted during predetermined acquisition windows based on cardiac measurements of the object of interest, a method commonly referred to as "cardiac gating."

Conventional cardiac gating technique are based on a user selected scan prescription before initiating the scan (e.g., injecting the contrast agent, begin acquiring imaging information), which defines pre-programmed rules for acquisition windows. For example, the user measures a heart rate or determines specific arrhythmia complexes based from initial cardiac measurements of the object of interest. The user uses one or more tables listing candidate scan prescriptions with corresponding heart rates or specific arrhythmia complexes. Based on the initial cardiac measurements and the one or more tables, the user selects an appropriate scan prescription.

However, once the scan prescription is selected the scan prescription cannot be changed during the scan reducing the success rate for the CT scan. For example, any changes to the cardiac behavior of the object of interest that is not pre-programmed within the scan prescription may result in blurred or invalid imaging information. Invalid imaging information may require additional CT scans for the object of interest resulting, which may be adverse to the health of the objection of interest, such as increased radiation exposure, increased chance of having an adverse reaction to the contrast agent, or the like. Thus, there is a need to adjust the scan prescription during the CT scan.

BRIEF DESCRIPTION OF THE INVENTION

In one embodiment, a method is provided that may include obtaining a scan prescription. The scan prescription may be based on an acquisition rule set. The method may also include, receiving physiologic features of interest (FOI) measurements of an object of interest during a scan time. The method further may include, comparing at least one of the received physiologic FOI measurements with the predetermined threshold range, and determining a scan setting by evaluating the acquisition rule set based on the physiologic FOI measurement.

In another embodiment, an imaging system is provided. The imaging system may include an acquisition unit that includes a computed tomography (CT) detector configured to collect imaging data of an object of interest during one or more acquisition windows within a scan time. The imaging system may also include, a physiologic sensor configured to acquire physiologic FOI measurements of the object of interest, and a processing unit. The processing unit includes at least one processor operably coupled to the acquisition unit. The processing unit may be configured to acquire initial physiologic FOI measurements from the physiologic sensor proximate to a scan time. The processing unit may also be configured to obtain a scan prescription. The scan prescription may be based on an acquisition rule set. The processing unit may also be configured to receive a physiologic FOI measurement during the scan time, and to compare the physiologic FOI measurement with a predetermined threshold range. Further, the processing unit may be configured to determine an updated scan setting based on the acquisition rule set if the physiologic FOI measurement is outside the predetermined threshold range.

In another embodiment, a tangible and non-transitory computer readable medium is provided. The tangible and non-transitory computer readable medium includes one or more computer software modules configured to direct one or more processors. The tangible and non-transitory computer readable medium may direct the one or more processors to obtain a scan prescription. The scan prescription may be based on an acquisition rule set. The acquisition rule set may include one or more rule sets that define one or more acquisition windows for a computed tomography (CT) detector. The tangible and non-transitory computer readable medium may also direct the one or more processors to receive physiologic feature of interest (FOI) measurements of an object of interest during a scan time. Also, the tangible and non-transitory computer readable medium may direct the one or more processors to compare at least one of the received physiologic FOI measurements with a predetermined threshold range, and to determine an updated scan setting based on the acquisition rule set if the physiologic FOI measurement is outside the predetermined threshold range.

DETAILED DESCRIPTION OF THE INVENTION

Figure 1:
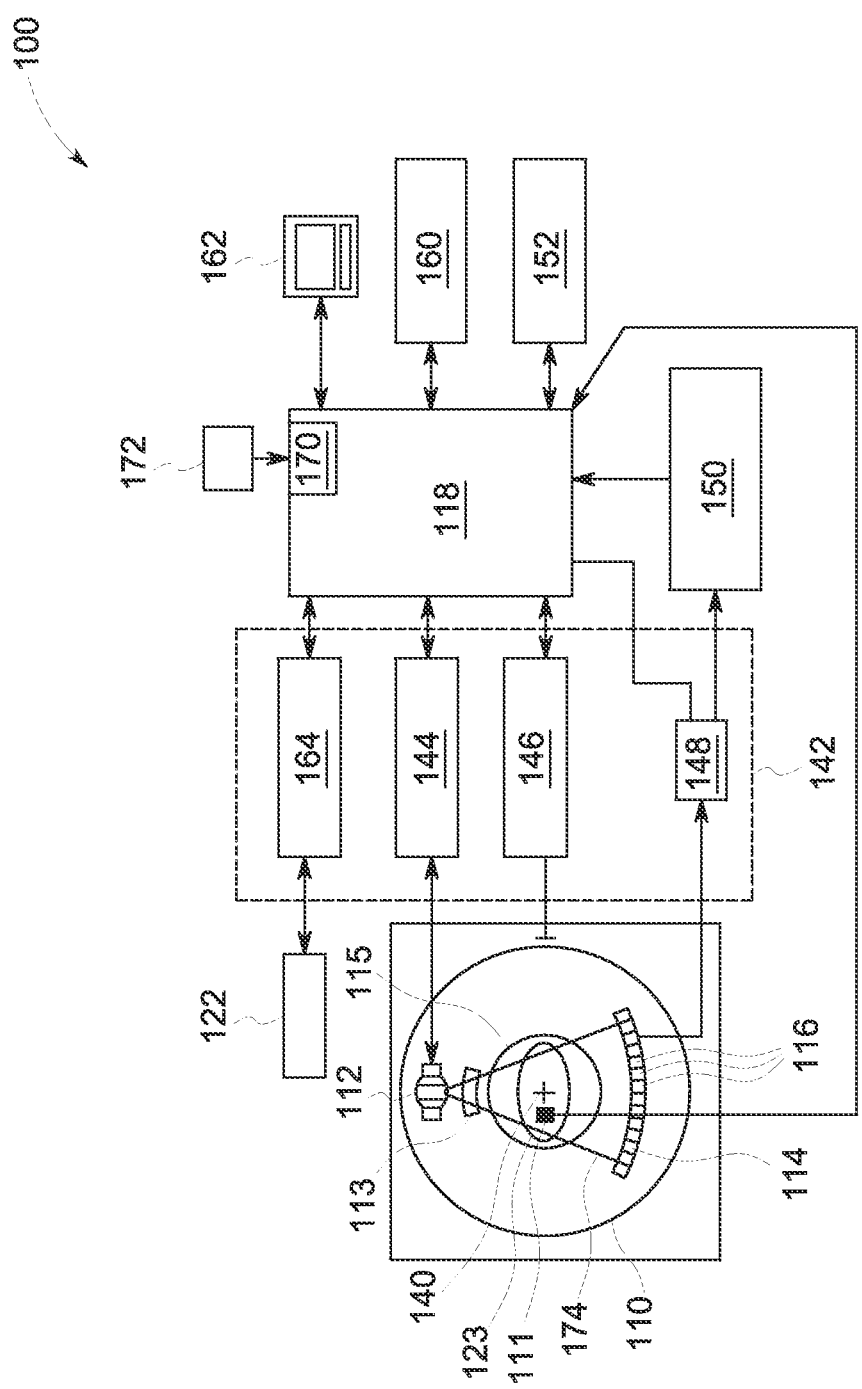
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for real-time adaptive acquisition control for imaging systems via multi-variable rule sets. Various embodiments provide a framework of tables allowing a user or clinician to develop a rule set to define how a gated (e.g., cardiac gated, electrocardiogram (ECG) gated, respiratory gated) scan prescription should be automatically adjusted based on physiologic measurements (e.g., heart rate, heart rate variability, arrhythmias, respiratory rate) of an object of interest (e.g., patient). In various embodiment, the rule set or a portion of the rule set may be sent and utilized by an acquisition subsystem. The acquisition subsystem may control how the X-ray controller, table motor controller, and/or gantry motor control adjusts and responds to changing physiologic conditions of the object of interest, such as heart rate, heart rate variability, detected irregularities or arrhythmia complexes.

A technical effect of at least one embodiment includes allowing gated scan acquisitions to change from a simple, fixed prescription to a more complex set of user-defined rules governing the scan acquisition in real time. For example, real-time acquisition parameters that could be adjusted or controlled real-time based on the rule set include: the desired acquisition phase(s), the amount of extra scan time (e.g. padding) to add before and after the exposure to account for heart rate prediction inaccuracy due to heart rate variation, whether the scan acquisition should allow for application of later motion correction algorithms, and rules defining when to automatically reacquire a scan.

A technical effect of at least one embodiment include allowing a user to specify responses to changing situations (e.g., changing physiologic measurements) during a scan. A technical effect of at least one embodiment includes increased imaging success rates reducing the need for additional CT scans and possible complications due to the additional CT scans (e.g., additional injections of contrast agent).

FIG. 1 illustrates a schematic diagram of an exemplary CT imaging system 100 that may be utilized to implement various embodiment discussed herein. Although the CT imaging system 100 is illustrated as a standalone imaging system, it should be noted that the CT imaging system 100 may form part of a multi-modality imaging system in some embodiments. For example, the multi-modality imaging system may include the CT imaging system 100 and a positron emission tomography (PET) imaging system, or a single photon emission computed tomography (SPECT) imaging system. It should also be understood that other imaging systems capable of performing the functions described herein are contemplated as being used.

The CT imaging system 100 includes a gantry 110 that has the X-ray source 112 that projects a beam of X-rays toward the detector array 114 on the opposite side of the gantry 110. A source collimator 113 and a bowtie filter module (not shown) are provided proximate the X-ray source 112. The detector array 114 includes a plurality of detector elements 116 that are arranged in rows and channels that together sense the projected X-rays that pass through an object of interest 123. The imaging system 100 includes a physiologic sensor 111 proximate to the object of interest 123. The physiologic sensor 111 such as an electrocardiogram (ECG), a respiratory sensor, or the like configured to acquire physiologic feature of interest (FOI) measurements of the object of interest 123. For example, the physiologic FOI measurement may be a heart rate, heart rate variability, amplitude of the R-peak, a heartbeat classification (e.g., outlier detection, irregularity classification), rate change, slop of the R-peak, morphology components (e.g., slope, amplitude, peak to peak) of or portions of a QRS complex or cardiac cycle, or the like. In another example, the physiologic FOI measurements may be a respiratory rate.

The imaging system 100 also includes a computer 118 that receives the projection data from the detector array 114 and processes the projection data to reconstruct an image of the object of interest 123. A motorized table 122 is utilized to move the object of interest 123 into and out of the gantry 110. Particularly, the table 122 moves at least a portion of the object of interest 123 through a gantry opening 115 that extends through the gantry 110. Further, the table 122 may be used to move the object of interest 123 vertically within the bore of the gantry 110.

The depicted detector array 114 includes a plurality of detector elements 116. Each detector element 116 produces an electrical signal, or output, that represents the intensity of an impinging X-ray beam and hence allows estimation of the attenuation of the beam as it passes through the object of interest 123. During a scan to acquire the X-ray projection data, the gantry 110 and the components mounted thereon rotate about a center of rotation 140. FIG. 1 shows only a single row of detector elements 116 (i.e., a detector row). However, the multi-slice detector array 114 includes a plurality of parallel detector rows of detector elements 116 such that projection data corresponding to a plurality of slices can be acquired simultaneously during a scan.

Rotation of the gantry 110, the operation of the X-ray source 112, and position of the motorized table 122 are governed by an acquisition subsystem 142 based on a scan prescription. The scan prescription may be stored on a storage device 152. The scan prescription defines the scan settings from an acquisition rule set, such as when the X-ray source 112 is activated for acquiring projection data. The acquisition rule set may be a collection of candidate scan settings with associated physiologic FOI measurements. The acquisition rule set may be used as a look up table by the acquisition subsystem 142 or a computer 118 to match a corresponding physiologic FOI measured by the physiologic sensor 111 with a corresponding scan setting. The acquisition rule set may be generated from user inputs from an operator console 160. Additionally or alternatively, the acquisition rule set may be generated from priori information (e.g., patient population acquisition studies, pre-programmed rule sets).

The acquisition subsystem 142 includes an X-ray controller 144 that provides power and timing signals to the X-ray source 112. The X-ray controller 144 may deliver power and/or instruct the X-ray source 112 to project X-rays during an acquisition window based on the scan settings defined by the scan prescription. The acquisition subsystem 143 also includes a gantry motor controller 146 that controls the rotational speed and position of the gantry 110. In addition, the acquisition subsystem 142 may also include a table motor controller 164 that controls the motorized table 122 to position the object of interest 123 in the gantry 110. Particularly, the motorized table 122 moves at least a portion of the object of interest 123 through the gantry opening.

A data acquisition system (DAS) 148 in the acquisition subsystem 142 samples analog data from detector elements 116 and converts the data to digital signals for subsequent processing. An image reconstructor 150 receives the sampled and digitized X-ray data from the DAS 148 and performs high-speed image reconstruction. The reconstructed images are input to the computer 118 that stores the image in a storage device 152. The computer 118 may also receive commands and scanning parameters, such as the scan prescription from an operator via a console 160 that has a keyboard. The operator supplied commands and parameters are used by the computer 118 to provide control signals and information to the acquisition subsystem for instructing the DAS 148, the X-ray controller 144, the gantry motor controller 146, and the table motor controller 164. An associated visual display unit 162 allows the operator to observe the reconstructed image and other data from computer. It may be noted that one or more of the computer 118, controllers, or the like.

In various embodiments, the computer 118 includes a device 170, for example, a CD-ROM drive, DVD drive, magnetic optical disk (MOD) device, or any other digital device including a network connecting device such as an Ethernet device for reading instructions and/or data from a tangible non-transitory computer-readable medium 172, that excludes signals, such as a CD-ROM, a DVD or another digital source such as a network or the Internet, as well as yet to be developed digital means. In another embodiment, the computer 118 executes instructions stored in firmware (not shown). The computer 118 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 112 and the detector array 114 are rotated with the gantry 110 within the imaging plane and around the subject 117 to be imaged such that the angle at which an X-ray beam 174 intersects the object of interest 123 constantly changes. A group of X-ray attenuation measurements, i.e., projection data, from the detector array 114 at one gantry angle is referred to as a "view" or "projection." A "scan" of the object of interest 123 comprises a set of views made at different gantry angles, or view angles, during one or more revolutions of the X-ray source 112 and the detector array 114. In a CT scan, the projection data is processed to reconstruct an image that corresponds to a three-dimensional volume taken of the subject 117. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

Figure 2:
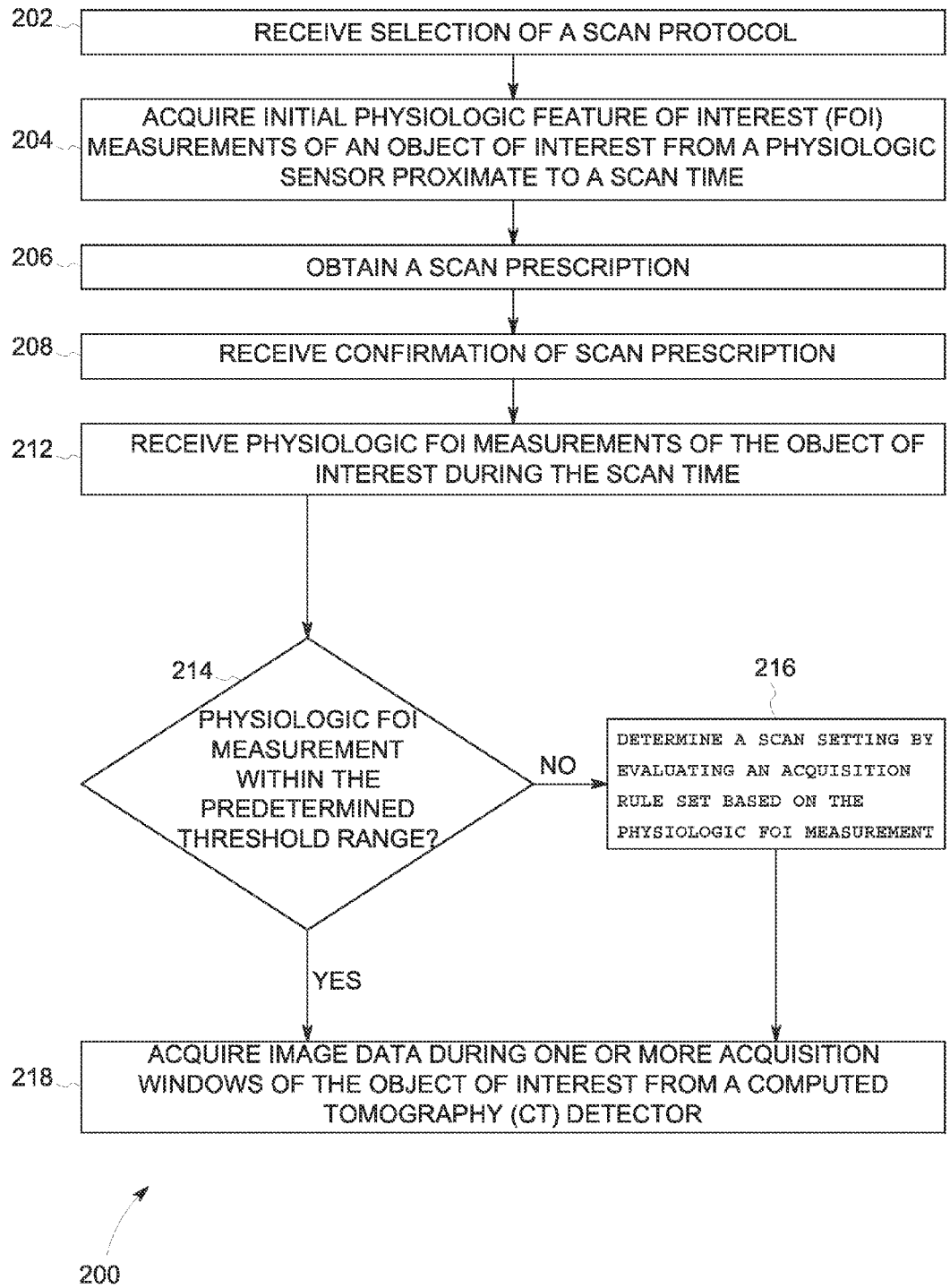
FIG. 2 is a flowchart of a method in accordance with various embodiments.

FIG. 2 illustrates a flowchart of a method 200 for real-time adaptive acquisition control for imaging systems. The method 200, for example, may employ structures or aspects of various embodiments (e.g., systems and/or methods) discussed herein, such as the CT imaging system 100. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be used as one or more algorithms to direct hardware to perform one or more operations described herein. It should be noted, other methods may be used, in accordance with embodiments herein.

One or more methods may (i) obtain a scan prescription; (ii) receive physiologic FOI measurements of an object of interest during a scan time; (iii) comparing at least one of the received physiologic FOI measurement with a predetermined threshold range; and (iv) determine a scan setting by evaluating the acquisition rule set based on the physiologic FOI measurement.

Beginning at 202, selection of a scan protocol may be received. The scan protocol may correspond to a region of interest or particular scan type to be performed on the object of interest 123. Based on the scan protocol the computer 118 may determine candidate scan prescriptions that may be used for the scan. For example, a user may select a coronary artery imaging protocol on the operator console 160. Since coronary artery imaging pertains to cardiac CT imaging, the computer 118 may select scan prescriptions that are based on physiologic FOI measurements that pertain to a heart rate, heart variability, or the like. In another example, the user may select a abdomen and pelvis CT imaging or lung CT imaging, the computer 118 may select scan prescription that are based on physiologic FOI measurements that pertain to a respiratory rate.

At 204, initial physiologic FOI measurement of the object of interest 123 may be acquired from a physiologic sensor 111 proximate to a scan time. The scan time may correspond to a period from injecting the contrasting agent into the object of interest until final image or projection data is acquired by the imaging system 100 of the object of interest.

Figure 3:
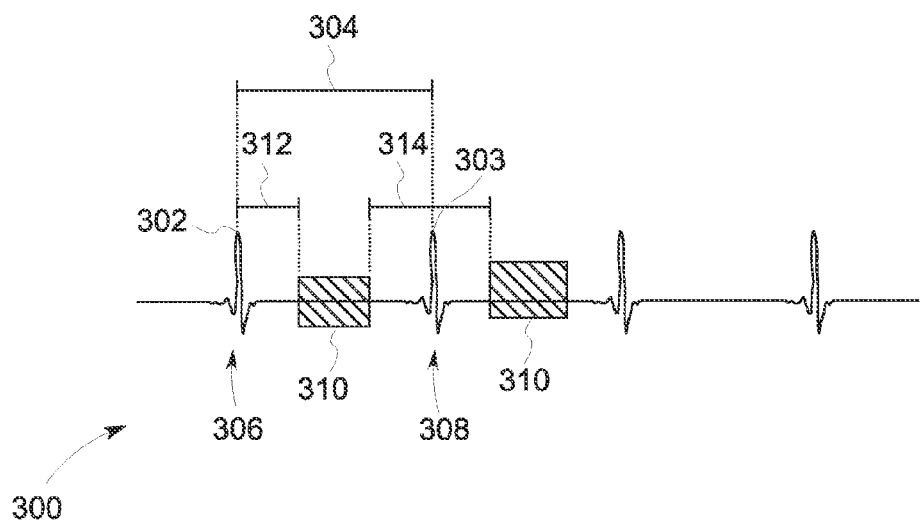
FIG. 3 is a graphical illustration of an exemplary physiologic signal from a physiologic sensor in accordance with various embodiments.

For example, the initial physiologic FOI measurement may be acquired within sixty minutes of the scan time or injection of the contrasting agent. Additionally or alternatively, the scan time may correspond to a period from confirmation of a scan prescription (e.g., at 208) until a final image or projection data is acquired by the imaging system 100. It should be noted that in various other embodiments the initial physiologic FOI measurements may be acquired within one hundred twenty minutes, ninety minutes, thirty minutes, twenty minutes, ten minutes, five minutes, or the like. The initial physiologic FOI measurements are further described in connection with FIG. 3. FIG. 3 is an exemplary physiologic signal 300 from the physiologic sensor 111 received by the computer 118.

The physiologic signal 300 graphically illustrates movement of the heart within the object of interest 123 during a cardiac cycle. As illustrated in FIG. 3, the cardiac cycle (e.g., a heartbeat) is typically defined by a pair of R-peaks 302-303 of adjacent QRS complexes, for example, the QRS complexes 306 and 308. The initial physiologic FOI measurement, for example, may be a heart rate determined by an R-R interval 304 from the physiologic signal 300 proximate to the scan time, such as before confirmation of the scan prescription at 208.

At 206, a scan prescription may be obtained. The scan prescription may define an initial scan setting based on the initial physiologic FOI measurements. The scan settings may correspond to one or more acquisition windows, number of scan positions (e.g., the relative position of the gantry 110 with respect to the object of interest 123), rotational speed of the gantry 110 during image acquisition, timing to move the motorized table to another scan position, inter-scan delay (e.g., time between the one or more acquisition windows), or the like. The scan prescription may be obtained or selected from the candidate scan prescriptions automatically by the computer 118 or selected manually from the user, based from an acquisition rule set. The acquisition rule set may include a database with one or more prescribed rule sets with corresponding scan prescriptions. Each rule set includes a scan setting defined by the corresponding scan prescription and a predetermined threshold range of a physiologic FOI measurement. The rule set may be selected when the initial physiologic FOI measurements is within the predetermined threshold range of the rule set. For example, the computer 118 may automatically select a scan prescription corresponding to a rule set with initial physiologic FOI measurements within the predetermined threshold range of the rule set.

The predetermined threshold range may correspond to a single physiologic FOI measurement. For example, the computer 118 may receive the initial physiologic FOI measurement of approximately 60 beats per minute or having the R-R interval 304 of approximately 1000 milliseconds. The computer 118 may compare the initial physiologic FOI measurement with the acquisition rule set to determine the acquisition window 310. The acquisition rule set may include a rule set with a scan setting for R-R intervals 304 within a predetermined threshold range of 950-1050 milliseconds, defining the acquisition window 310. The computer 118 determines that the initial physiologic FOI is within the predetermined threshold range and selects the scan settings of the rule set.

Additionally or alternatively, the predetermined threshold range may correspond to multiple physiologic FOI measurements, such as a heart rate variability. For example, the predetermined threshold range may be based on a maximum and minimum average R-R interval determined from multiple physiologic FOI measurements (e.g., multiple R-intervals 304). In at least one embodiment the predetermined threshold range may be based on more than one characteristic of the physiologic FOI. For example, the acquisition rule set may include a rule set based on the R-R interval 304 and an amplitude of the R-peak 302. The predetermined threshold range of the rule set may include a maximum and minimum size of the R-R interval 304 and a maximum and minimum size of the R-peak 302.

In at least one embodiment, the predetermined threshold range may be based on a physiologic FOI template, for example, to classify the heartbeat. The computer 118 may compare and valuate differences (e.g., determining a correlation value, area of difference, match percentage) in the morphology between the initial physiologic FOI with one or more physiologic FOI templates. The physiologic FOI templates may correspond to heart beat classifications, such as various arrhythmia complexes (e.g., premature ventricular complexes (PVC) or irregularity classifications, premature junctional complexes, premature atrial complexes, bigeminy, trigeminy), respiratory breathing pattern, outlier detection, or the like. One of the rule sets may define a predetermined threshold range corresponding to a value of the valuated differences. For example, the computer 118 may receive an initial physiologic FOI measurements the QRS complex 306. The computer 118 may compare the QRS complex 306 with physiologic FOI templates of different rule sets on the acquisition rule set, and determine, for example, a match percentage representing a percentage a morphology of the QRS complex 306 is similar to the physiologic FOI templates. Each of the rule sets may have a predetermined threshold range that includes a minimum match value. The computer 118 may automatically select the rule set that includes a physiologic FOI template where the match value of the QRS complex 306 is within the predetermined threshold range and/or has the highest match value.

Additionally or alternatively, the acquisition rule set may include rule sets based on irregularities in the initial physiologic FOI measurement. For example, the rule set may include scan settings where an arrhythmia complex occurred during the initial physiologic FOI measurement. Other examples of rule sets for determining the acquisition window and scan settings based on, specifically, cardiac measurements is disclosed in U.S. Pat. No. 7,558,363, entitled "Step-and-shoot cardiac CT imaging," which is expressly incorporated herein by reference in its entirety.

The acquisition window 310 is defined within each R-R interval 304 to reduce motion artifacts in the projection data corresponding to motion of the heart. The size (e.g., amount of time) of the acquisition window 310 may be based on a percentage of the R-R interval 304, for example, 10%. It should be noted that the size of the acquisition window 310 may be greater than 10% of the R-R interval 304 or less than 10% of the R-R interval. Optionally, the start of the acquisition window 310 may be based on a delay time 312 relative to the first R-wave 302 of the R-R interval 304. Additionally or alternatively, the end of the acquisition window 310 may be based on a buffer time 313 relative to the second R-wave 303 of the R-R interval 304.

X-rays are projected toward the object of interest 123 during the acquisition window 310. Particularly, the X-ray controller 144 of the acquisition subsystem 142 will power or instruct the X-ray source 112 to emit X-rays during the acquisition window 310. X-ray emission is disabled during other periods of the R-R interval 304. The acquisition window 310 may correspond to a phase of the heart during which data acquisition is to occur. During phases of the cardiac cycle in which data acquisition is not to occur, the X-ray source 112 is controlled by the X-ray controller 144 to not project X-rays toward the object of interest 123. Two adjacent acquisition windows 310 can form an inter-scan delay 314 which may be used by the acquisition subsystem 142 to move one or more of the object of interest 123, the motorized table 122, and/or the gantry 110 to the next scanning position for a subsequent acquisition window.

At 208, a confirmation of a scan prescription may be received. For example, once the scan prescription is obtained either automatically by the computer 118 or manually by the user, the user may confirm the scan prescription and/or scan settings. Additionally or alternatively, the user may also confirm the rule set corresponding to the obtained scan prescription automatically selected based from the acquisition rule set on the operator console 160. When the scan prescription is confirmed, the computer 118 may instruct the acquisition subsystem 142, for example, to adjust at least one of the table 122 (e.g., instruct the table motor control 164 to position the object of interest 123 to a first scan position) or the gantry 110 (e.g., to positioned the X-ray source 112 and the detector array 114), corresponding to initial scan settings defined by the confirmed scan prescription. Optionally, the scan time may be started when the scan prescription is confirmed. Additionally or alternatively, a contrast agent may be injected into the object of interest 123 when the scan prescription is confirmed.

At 212, physiologic FOI measurements of the object of interest may be received during the scan time. For example, physiologic FOI measurements may be received by the computer 118 from the physiologic sensor 111 at predetermined periods during the scan time, continually (e.g., in real time) during the scan time, or the like.

At 214, the method 200 may determine whether the physiologic FOI measurement is within the predetermined threshold range. The predetermined threshold range may be defined from the selected rule set in the acquisition rule set at 208. The computer 118 may compare one or more of the physiologic FOI measurements acquired during the scan time, to determine if the physiologic FOI measurements are within the predetermined threshold range of the rule set corresponding to the scan prescription selected at 208. Optionally, the computer 118 may compare a physiologic FOI measurement during a predetermined cycle based on a comparison of a previous physiologic FOI measurement. For example, the computer 118 may compare a received physiologic FOI measurement when the previously received physiologic FOI measurements has been compared by the computer 118. In at least one embodiment, the computer 118 may compare each physiologic FOI measurement once received from the physiologic sensor 111.

Figure 4:
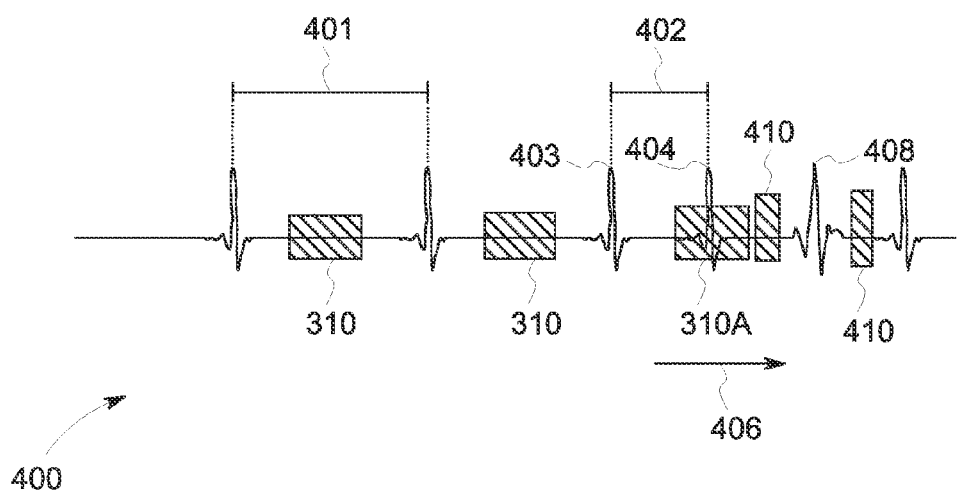
FIG. 4 is a graphical illustration of an exemplary physiologic signal from a physiologic sensor in accordance with various embodiments.

For example, the selected scan settings is based on a rule set having a predetermined threshold range based on a physiologic FOI of an R-R interval 401 (e.g., heart rate) between 950-1050 milliseconds. An R-R interval 402 of 650 milliseconds, formed by R-peaks 403, 404, is measured by the physiologic sensor 111 during the scan time and shown in the physiologic signal 400 graphically illustrated in FIG. 4. The computer 118 may compare the R-R interval 402 with the predetermined threshold range, and determine that the physiologic FOI of the R-R interval 402 is not within the predetermined threshold range of 950-1050 milliseconds.

If the physiologic FOI measurement is not within the predetermined threshold range, at 216, an updated scan prescription or scan setting may be determined based on the acquisition rule set. For example, the method may determine a scan setting by evaluating the acquisition rule set based on the physiologic FOI measurement. In at least one embodiment, when the computer 118 determines that the physiologic FOI measurement is not within the predetermined threshold range, the computer 118 may compare the received physiologic FOI measurement with the acquisition rule set to select a new rule set with a corresponding scan prescription defining new scan settings.

For example, the computer 118 may determine that the R-R interval 402 is not within the predetermined threshold range based from a rule set selected based on an initial physiologic FOI measurement, such as the R-R interval 401. The computer 118 may compare the R-R interval 402 with the predetermined acquisition ranges of other rule sets in the acquisition rule set. The computer 118 may select a new rule set with the R-R interval 402 within a predetermined threshold range of the new rule set. The new rule set may include scan settings defined by a corresponding scan prescription, which is used by the computer 118 to update the scan settings used for acquiring image data of the object of interest 123. Once the updated scan settings are selected, the computer 118 may update the predetermined threshold range for subsequent physiologic FOI measurements during the scan time to the predetermined threshold range of the new rule set.

The updated scan settings may also include re-acquiring image data of the object of interest 123 corresponding to the image data previously acquired in the acquisition window 310*a* based on the physiologic FOI measurement. For example, the reduced size of the R-R interval 402 results in the R-peak 404 occurring during the acquisition window 310*a*, which may result in increased motion artifacts in the image data. Once the updated scan settings are selected, the computer 118 may instruct the acquisition subsystem 142 to hold the scan position (e.g., not activating the table motor controller 164 and/or the gantry motor controller 146 to move the object of interest 123 to another scan position) of the object of interest 123 after the acquisition window 310*a* is completed, and acquire image or projection data at the acquisition window 410 corresponding to the updated scan settings.

Additionally or alternatively, the updated scan setting may include adjusting the acquisition window 310*a* to apply motion correction post processing to the acquired image data due. For example, the updated scan settings may increase the size of the acquisition window 310*a* by moving the end time of the acquisition window 310*a* in the direction of an arrow 406 towards the subsequent R-peak 408, which increases an amount of image data acquired during the acquisition window 310*a*. The additional image data may be used by motion correction algorithms (e.g., SnapShot Freeze) to reduce and/or remove motion artifacts in the image data acquired during the acquisition window 310*a*. The new scan settings, for example, may include reducing the size of the acquisition window 310 to form the acquisition window 410. It should be noted, in other embodiments the updated scan settings may increase the size of the acquisition window 310.

Additionally or alternatively, the new scan settings may include selecting a different phase of the cardiac cycle. For example, the new scan settings may adjust a position of the acquisition window 310 relative to the received physiologic FOI measurement, such as moving a position of the acquisition window within the R-R interval 401 (e.g., equally adjusting a position of the start and stop time of the acquisition window 310 within the R-R interval 401).

Figure 5:
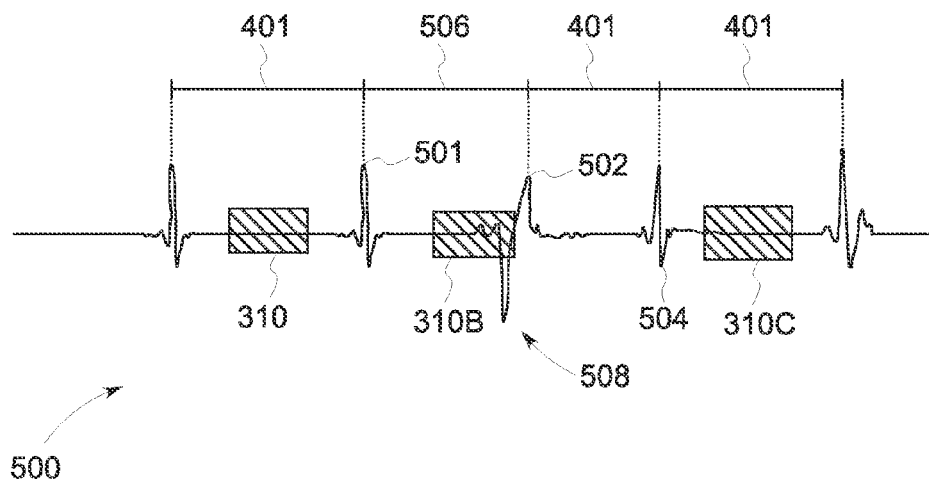
FIG. 5 is a graphical illustration of an exemplary physiologic signal from a physiologic sensor in accordance with various embodiments.

In another example, an R-R interval 506, formed by R-peaks 501 and 502 is measured by the physiologic sensor 111 during the scan time and shown in the physiologic signal 500 graphically illustrated in FIG. 5. The computer 118 may compare the R-R interval 506 with the predetermined threshold range, and determine that the physiologic FOI of the R-R interval 506 is not within the predetermined threshold range. The computer 118 may also determine that the R-peak 501 is a part of an arrhythmia complex, such as a PVC, based on one or more features of the morphology (e.g., change in amplitude of the R-peak 502 relative to the previous R-peak 501, length in time of cardiac cycle 508, match percentage of the cardiac cycle 508 with an arrhythmia template) of the cardiac cycle 506. When the computer 118 determines the presence of a PVC, the computer 118 may update the scan settings based on a rule set of the acquisition rule set corresponding to PVC. For example, the updated scan settings may have the computer 118 instruct the acquisition subsystem 142 to re-acquire the image data acquired during the acquisition window 310b at an acquisition window 310c when an arrhythmia complex is no longer detected by the computer 118 (e.g., detection of QRS complex 504). In another example, the updated scan settings for a detected arrhythmia complex may adjust the size (e.g., increase, decrease) of the acquisition window 310. Additionally or alternatively, the updated scan settings for a detected arrhythmia complex may increase the size of the acquisition window 310 for motion correction algorithms. It should be noted that the acquisition rule set may include other rule sets corresponding to other arrhythmia complexes, such as premature junctional complexes, premature atrial complexes, bigeminy, trigemini, or the like.

Optionally, the computer 118 may add extra scan time or padding (e.g., increase the size of the acquisition window 310) even if the physiologic FOI measurement acquired during the scan time is within the predetermined threshold range. For example, if the computer 118 measures variations in the physiologic FOI measurement, such as due to variations of the heart rate or respiratory rates, over a predetermined time the computer 118, based on the rule set, may adjust the acquisition window 310 to account for prediction inaccuracy of the physiologic FOI.

At 218, image data may be acquired during one or more acquisition windows (e.g., 310, 410) of the object of interest 123 from a CT detector 114. The one or more acquisition windows are within the scan time defined by the scan prescription (e.g., the initial scan settings, the updated scan settings).

Figure 6:
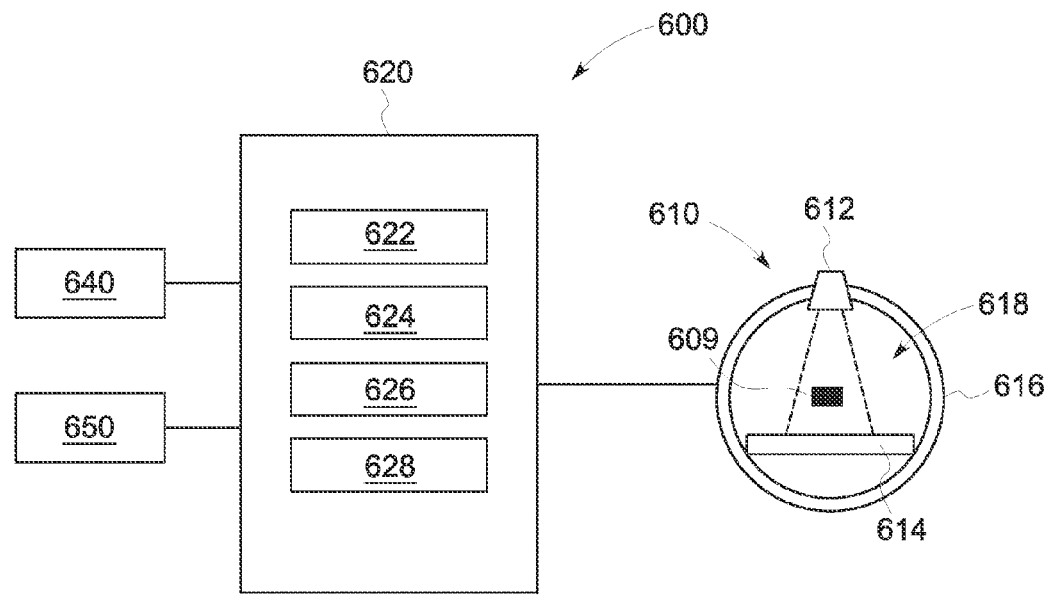
FIG. 6 is a schematic block diagram of a computed tomography (CT) imaging system in accordance with an embodiment.

FIG. 6 illustrates an imaging system 600 in accordance with an embodiment. The imaging system 600 may be utilized to perform or implement one or more aspects of the method 200 discussed herein, for example. The imaging system 600 may be configured, for example, to perform computed tomography (CT) scanning of an object, such as a human or animal patient (or portion thereof). The imaging system 600 includes a CT acquisition unit 610 (e.g., acquisition subsystem 142) and a processing unit 620. Generally, the CT acquisition unit 610 is configured to acquire projection data or imaging data, and the processing unit 620 is configured to reconstruct images using the data acquired by the CT acquisition unit 610. It may be noted that various embodiments may include additional components, or may not include all of the components shown in FIG. 6 (for example, various embodiments may provide sub-systems for use with other sub-systems to provide an imaging system). Further, it may be noted that certain aspects of the imaging system 600 shown as separate blocks in FIG. 6 may be incorporated into a single physical entity, and/or aspects shown as a single block in FIG. 6 may be shared or divided among two or more physical entities.

The depicted CT acquisition unit 610 includes an X-ray source 612 and a CT detector 614. The X-ray source 612 and the CT detector 614 (along with associated components such as bowtie filters, source collimators, detector collimators, or the like (not shown in FIG. 6)) may rotate about a central axis of a bore of a gantry 616 of the system 600. The acquisition unit 610 includes a physiologic sensor 609 proximate to the object being scanned. The physiologic sensor 609 such as an electrocardiogram (ECG), a respiratory sensor, or the like configured to acquire physiologic FOI measurements of the object.

Generally, X-rays from the X-ray source 612 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 612 to control distribution of X-rays passed to the object to be imaged.

X-rays that pass through the object to be imaged are attenuated by the object and received by the CT detector 614 (which may have a detector collimator associated therewith), which detects the attenuated X-rays and provides imaging information to the processing unit 620. The processing unit 620 may then reconstruct an image of the scanned portion of the object using the imaging information (or projection information) provided by the CT detector 614. The processing unit 620 may include or be operably coupled to the output unit 640, which in the illustrated embodiment is configured to display an image, for example, an image reconstructed by the processing unit 620 using imaging information from the CT detector 614 acquired during a scan time. The depicted input unit 650 is configured to obtain input corresponding to a scan to be performed, with the processing unit 620 using the input to determine one or more scan prescriptions defining scan settings (e.g., tube voltage, tube current, scanning rotation speed, acquisition windows, or the like). The input unit 650 may include a keyboard, mouse, touchscreen or the like to receive input from an operator, and/or may include a port or other connectivity device to receive input from a computer or other source.

In the illustrated embodiment, the X-ray source 612 is configured to rotate about the object. For example, the X-ray source 612 and the CT detector 614 may be positioned about a bore 618 of the gantry 616 and rotated about the object to be imaged. As the X-ray source 612 rotates about the object during an imaging scan, X-rays received by the CT detector 614 during one complete rotation provide a 360 degree view of X-rays that have passed through the object. Other imaging scanning ranges may be used in alternative embodiments. The CT imaging information may be collected as a series of views that together make up a rotation or portion thereof. Each view or projection may have a view duration during which information (e.g., counts) is collected for the particular view. The view duration for a particular view defines a CT information acquisition period or acquisition window for that particular view. For example, in embodiments having 1000 views or projections per rotation, and with the gantry rotating at a constant speed, the X-ray source may be left on for 1/1000 of the time of a complete rotation to acquire a single view or projection of CT information. A blanking interval may separate a first view or projection from the next view or projection in the series.

As indicated herein, the processing unit 620 is configured to control various aspects of the acquisition units and/or to reconstruct an image using information obtained via the acquisition units. For example, the processing unit 620 may be configured to reconstruct a CT image using information collected by the CT acquisition unit 610. The processing unit 620 of the illustrated embodiment is configured to perform one or more aspects discussed in connection with the method 600 (e.g., obtaining a scan prescription that defines an initial scan setting based on an initial physiologic FIO of an object of interest, receiving physiologic FOI measurements of an object of interest during a scan time, comparing at least one of the received physiologic FOI measurements with a predetermined threshold range, determining an updated scan setting based on an acquisition rule set if the physiologic FOI measurement is outside the predetermined threshold range).

The depicted processing unit 620 is operably coupled to the input unit 650, the output unit 640, and the CT acquisition unit 610. The processing unit 620, for example, may receive imaging data or projection data from the CT detector 614. As another example, the processing unit 620 may provide control signals to one or more aspects of the CT acquisition unit 610, such as the X-ray source 612 and CT detector 614. The processing unit 620 may include processing circuitry configured to perform one or more tasks, functions, or steps discussed herein. It may be noted that "processing unit" as used herein is not intended to necessarily be limited to a single processor or computer. For example, the processing unit 620 may include multiple processors and/or computers, which may be integrated in a common housing or unit, or which may distributed among various units or housings. It may be noted that operations performed by the processing unit 620 (e.g., operations corresponding to process flows or methods discussed herein, or aspects thereof) may be sufficiently complex that the operations may not be performed by a human being within a reasonable time period. For example, the processing of imaging data, control of an imaging acquisition unit, or performance of filtering, back projection, linear transforms, or inverse linear transforms may rely on or utilize computations that may not be completed by a person within a reasonable time period.

The depicted processing unit 620 is configured to control the CT acquisition unit 610 to collect dual-energy CT information during an imaging scan.

The processing unit 620 includes a reconstruction module 622, a determination module 624, a control module 626, and a memory 628. It may be noted that other types, numbers, or combinations of modules may be employed in alternate embodiments, and/or various aspects of modules described herein may be utilized in connection with different modules additionally or alternatively. Generally, the various aspects of the processing unit 620 act individually or cooperatively with other aspects to perform one or more aspects of the methods, steps, or processes discussed herein.

The depicted reconstruction module 622 is configured to reconstruct one or more images using imaging or projection data acquired from the CT detector 614. For example, the reconstruction module 622 may receive imaging information from the CT detector 614 taken over a number of views (e.g., for a full rotation or portion thereof, or for a number of rotations taken at different positions along the length of an object to be imaged) and reconstruct an image used for diagnostic purposes.

In the illustrated embodiment, the determination module 624 is configured to receive information from the CT acquisition unit 610 (e.g., CT information for a reference projection, candidate projections, physiologic FOI measurements and/or one or more sample projections) and/or the input unit 650 (e.g., information describing or corresponding to a patient, procedure, or scanning parameters). The determination module 624 may automatically obtain a scan prescription that defines the initial scan settings based on physiologic FOI measurements received from the physiologic sensor 409. The determination module 620 may also compare one or more of physiologic FOI measurements received during a scan time with predetermined threshold ranges. The determination module 620 may also determine an updated scan setting based on the acquisition rule set if the physiologic FOI measurement is outside the predetermined threshold range.

The depicted control module 626 is configured to control the CT acquisition unit 610 and/or other aspects of the system 600 to collect spectral CT projection data or information based on the scan settings selected by the determination module 624.

The memory 628 may include one or more computer readable storage media. The memory 628, for example, may store acquired CT information, the scan prescription, the acquisition rule set, values of parameters to be used in performing various aspects of the process flows or methods discussed herein, image data corresponding to images generated, results of intermediate processing steps, or the like. Further, the process flows and/or flowcharts discussed herein (or aspects thereof) may represent one or more sets of instructions that are stored in the memory 628 for direction operations of the system 600.

The output unit 640 is configured to provide information to the user. The output unit 660 may be configured to display, for example, one or more material images, de-noised material images, or de-noised synthetic monochromatic images, among others. The output unit 660 may include one or more of a screen, a touchscreen, a printer, or the like.

The input unit 650 may be configured to obtain an input that corresponds to one or more settings or characteristics of a scan to be performed, and to provide the input (or information corresponding to the input) to the processing unit 620, which may use the input to determine, adjust, or select the one or more parameters to be used in acquiring or processing imaging data. The input may include, for example, a portion of the body to be scanned (e.g., head, body). As another example, the input may include one or more parameter values to be used for guided de-noising, and/or information from which one or more such parameter values may be determined. The input unit 650 may be configured to accept a manual user input, such as via a touchscreen, keyboard, mouse, or the like. Additionally or alternatively, the input unit 650 may receive information from another aspect of the imaging system 600, another system, or a remote computer, for example, via a port or other connectivity device. The input unit 650 may also be configured to obtain user approval or denial of a proposed scanning setting.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
   obtaining a scan prescription;
   receiving physiologic FOI measurements of an object of interest during a scan time;
   comparing at least one of the received physiologic FOI measurements with a predetermined threshold range; and
   determining a scan setting by evaluating an acquisition rule set based on the physiologic FOI measurement.

2. The method of claim 1, further comprising acquiring image data during one or more acquisition windows of the object of interest from a computed tomography (CT) detector based on the scan setting, wherein the one or more acquisition windows are within the scan time and defined by the acquisition rule set.

3. The method of claim 1, wherein the scan setting includes instructing a computed tomography (CT) detector to re-acquire image data of the object of interest corresponding to image data previously acquired by the CT detector based on the at least one of the received physiologic FOI measurements.

4. The method of claim 1, wherein the scan setting includes adjusting a size of an acquisition window.

5. The method of claim 1, wherein the scan setting includes adjusting a position of an acquisition window relative to the at least one received physiologic FOI measurements.

6. The method of claim 1, wherein the scan setting includes adjusting an acquisition window to allow or facilitate application of motion correction post processing to image data acquired during the acquisition window.

7. The method of claim 1, wherein an initial physiologic FOI and the physiologic FOI measurements correspond to at least one of a heart rate, a heart rate variability rate, a heartbeat classification, a rate of change.

8. The method of claim 7, further comprises determining an arrhythmia complex based on the at least one of the received physiologic FOI measurement corresponding to the heartbeat classification, wherein the acquisition rule set defines scan settings corresponding to one or more types of arrhythmia complexes.

9. The method of claim 1, further comprising adjusting the predetermined threshold range during the scan time based on a plurality of the physiologic FOI measurements.

10. An imaging system comprising:
an acquisition unit comprising a computed tomography (CT) detector configured to collect imaging data of an object of interest during one or more acquisition windows within a scan time;
a physiologic sensor configured to acquire physiologic FOI measurements of the object of interest; and
a processing unit comprising at least one processor operably coupled to the acquisition unit, the processing unit configured to:
acquire initial physiologic FOI measurements from the physiologic sensor proximate to a scan time;
obtain a scan prescription;
receive a physiologic FOI measurement during a scan time;
compare the physiologic FOI measurement with a predetermined threshold range; and
determine an updated scan setting based on an acquisition rule set if the physiologic FOI measurement is outside the predetermined threshold range.

11. The imaging system of claim 10, wherein the updated scan setting includes instructing the acquisition unit to re-acquire image data of the object of interest corresponding to image data previously acquired by the acquisition unit.

12. The imaging system of claim 10, wherein the processing unit is configured to instruct the acquisition unit to adjust a size of the acquisition window based on the updated scan setting.

13. The imaging system of claim 10, wherein the processing unit is configured to instruct the acquisition unit to adjust a position of an acquisition window relative to the physiologic FOI measurement.

14. The imaging system of claim 10, wherein the physiologic sensor is configured to measure cardiac electric signals, the initial physiologic FOI and the physiologic FOI measurement correspond to at least one of a heart rate, a heart rate variability rate, a heartbeat classification, rate of change.

15. The imaging system of claim 14, further comprises determining an arrhythmia complex based on the physiologic FOI measurement corresponding to the heartbeat classification, wherein the acquisition rule set defines scan settings corresponding to one or more types of arrhythmia complexes.

16. A tangible and non-transitory computer readable medium comprising one or more computer software modules configured to direct one or more processors to:
obtain a scan prescription, wherein the scan prescription defines one or more acquisition windows for a computed tomography (CT) detector;
receive physiologic feature of interest (FOI) measurements of an object of interest during a scan time;
compare at least one of the received physiologic FOI measurements with a predetermined threshold range; and
determine an updated scan setting based from an acquisition rule set if the physiologic FOI measurement is outside the predetermined threshold range.

17. The tangible and non-transitory computer readable medium of claim 16, wherein the updated scan setting adjusts at least one of a size of the one or more acquisition windows or a position of the one or more acquisition windows relative to the at least one of the received physiologic FOI measurements.

18. The tangible and non-transitory computer readable medium of claim 16, wherein an initial physiologic FOI and the physiologic FOI measurements correspond to at least one of a heart rate, a heart rate variability rate, heart beat classification, rate of change.

19. The tangible and non-transitory computer readable medium of claim 18, wherein the computer readable medium is further configured to direct the one or more processors to determine an arrhythmia complex based on the at least one of the received physiologic FOI measurements, wherein the acquisition rule set defines scan settings corresponding to one or more types of arrhythmia complexes.

20. The tangible and non-transitory computer readable medium of claim 16, wherein the computer readable medium is further configured to direct the one or more processors to instruct the CT detector to re-acquire image data of the object of interest corresponding to image data previously acquired by the CT detector based on the at least one of the received physiologic FOI measurements.

* * * * *